United States Patent [19]

Wisman et al.

[11] Patent Number: 4,573,997
[45] Date of Patent: Mar. 4, 1986

[54] RIGHT VENTRICULAR ASSIST DEVICE

[75] Inventors: Craig B. Wisman, Harrisburg; William Pierce, Hummelstown; James H. Donachy, Annville, all of Pa.

[73] Assignee: Research Corporation, New York, N.Y.

[21] Appl. No.: 590,813

[22] Filed: Mar. 19, 1984

[51] Int. Cl.⁴ .............................................. A61F 2/22
[52] U.S. Cl. .................................................... 623/3
[58] Field of Search ............................ 3/1.7; 128/1 D

[56] References Cited

U.S. PATENT DOCUMENTS

| | | | |
|---|---|---|---|
| 4,034,742 | 7/1977 | Thoma | 3/1.7 |
| 4,222,127 | 9/1980 | Donachy et al. | 128/1 D |
| 4,240,409 | 12/1980 | Robinson et al. | 3/1.7 |

Primary Examiner—Richard J. Apley
Assistant Examiner—James Prizant
Attorney, Agent, or Firm—Scully, Scott, Murphy & Presser

[57] ABSTRACT

A right ventricular assist device for assisting the circulation of the blood includes a smooth segmented polyurethane sac having a single valveless passageway to provide a single inlet and outlet. A rigid ellipsoidal shell surrounds the sac and has a first opening for the single valveless passageway and a second opening for pressurizing an interior portion of the shell. A flexible diaphragm extends across the interior of the shell and divides the interior into two unequal volumes; the sac and first opening in a first and larger volume, and a second opening and a pressurizing chamber in a second and smaller volume. The diaphragm is angled and dimensioned to expel up to 90% of the blood present in the sac by pressure supplied through the second opening. A vascular graft is attached between the valveless passageway and a pulmonary artery. Alternately, the sac may be formed with an elongate neck which is reinforced with a dacron graft anastomosed to the pulmonary artery.

15 Claims, 5 Drawing Figures

RIGHT VENTRICULAR ASSIST DEVICE

FIELD OF THE INVENTION

The invention relates to an artificial blood pump for assisting the circulation of blood from the right ventricle until the patient's heart recovers sufficiently to remove the assist device.

BACKGROUND OF THE INVENTION

Long term mechanical support of the heart has become a clinical reality during the past few years. Several devices are presently available that are capable of various degrees of left ventricular assistance. The intra-aortic balloon, now in widespread use, provides limited but frequently sufficient support for left ventricular heart failure of a mild nature. In addition, ventricular assist pumps are capable of providing circulatory support in the presence of severe left ventricular failure. Clinical experience with ventricular assist pumps have revealed multiple incidents where right ventricular failure has been present either concomitant with left ventricular failure or as an isolated entity. When present, right ventricular failure unresponsive to volume loading and inotropic drugs is frequently fatal.

Several instances of assisting the right ventricular function with a modified left ventricular assist pump have been reported, although in most cases, the patients have died. In addition, one instance of clinical right ventricular support has been reported in one case by utilizing an intra-aortic balloon in a vascular graft anastomosed to the pulmonary artery. However, despite a few reported successful cases of mechanical support of a failed right ventricle, the devices used have been cumbersome, and if coupled with a left ventricular assist pump for biventricle failure, can cause excessive blood trauma as well as compression of vital structures in the heart.

DESCRIPTION OF THE PRIOR ART

U.S. Pat. No. 4,222,127 entitled Blood Pump and Method of Pumping Blood which issued to two of the present co-inventors, discloses a blood pump for implant or paracorporeal use having a rigid case defining a pumping cavity with inlet and outlet valves, an integral thin walled flexible sac, a flexible diaphragm within the cavity conforming to the shape of the adjacent side of the sac and a control ring projecting into the cavity between the diaphragm and the sac to prevent complete ejection of the blood. The diaphragm is moved between diastolic and systolic positions to pump blood through the valves. In addition, portions of the sac are thickened and reinforced to prevent premature collapse of the sac around the discharge opening, and to provide a means for progressively collapsing the sac towards the outlet port.

U.S. Pat. No. 4,240,409 discloses an apparatus for mechanically assisting circulation of the blood in a patient for periods of up to a week or two until the patient's heart strengthens sufficiently to take over the full work load. The circulatory assist device includes a valveless pump with a flexible bladder and a pneumatic driver for collapsing the bladder. Because of its size and construction, it is primarily intended for paracorporeal support, and is not suitable for implanting within the human body.

U.S. Pat. No. 4,034,742 also discloses an apparatus for mechanically assisting circulation of the blood in the human body. In addition to the single valveless passageway and the flexible pumping chamber, this device requires a valve or blocking member to prevent the back flow of blood from the pumping chamber in the cardiovascular system. As described, the device is particularly adapted for assisting the left ventricle by installation in the aorta. No method or means is disclosed for installing the device in the somewhat limited space of the trunk of the pulmonary artery for use in assisting the right ventricle.

The use of balloon counter pulsation for acute right ventricle failure was disclosed in an article entitled "Pulmonary Artery Balloon Counter Pulsation For Acute Right Ventricle Failure" published in the Journal For Thoracic And Cardiovascular Surgery 80: 760–763, 1980. In this article, a balloon was installed in a tubular graft which was an anastomosed to the main pulmonary artery. In addition, a 35 ml unidirectional intra-aortic balloon was located in the conventional position in the descending aorta. The patient did not survive. The concept of arterial counter pulsation and intra-aortic balloon pumping for improving both right and left ventricle functions in an open chest setting was described in an article entitled "A New Counter Pulsation Device For The Treatment Of Acute Pulmonary Embolus Canine Circulatory Dynamics" described in volume 23 of the Transactions Of The American Society Of Artificial Internal Organs, pp. 103–108, 1977.

A complete bypass of the right ventricle to assist pulmonary circulation for a patient with right ventricular failure was disclosed in an article entitled "Ventricular Assist Pumping In Patients With Cardiogenic Shock After Cardiac Operations" in the New England Journal Of Medicine, volume 305, pp.1606–1610, 1981.

SUMMARY OF THE INVENTION

The right ventricular assist device disclosed herein is an effective device for supporting a weak or failing right ventricle. The device is simple in construction and operation. The device can be employed rapidly in a clinical setting using standard surgical techniques. The absence of mechanical valves results in extremely low levels of blood trauma. The design of the device and the materials used in its construction obviate the need for anti-coagulation medication while the device is in place. In addition, the device is sized and configured in such a way that it will not compress or compromise intrathoracic structures, even when employed in addition to a left ventricular assist pump.

The invention utilizes a smooth segmented polyurethane sac housed in a rigid plastic casing. The sac is an oblate spheroid with a single inlet and outlet passageway. Two means are disclosed for attaching the sac to the main pulmonary artery. In one means, provision is made for the attachment of a vascular graft to the passageway. The graft is then anastomosed to the main pulmonary artery in an end to side fashion. Alternately, the smooth segmented polyurethane sac may be formed with an elongate neck which is subsequently reinforced with a dacron graft, and the combined structure is then anastomosed to the main pulmonary artery in an end to side fashion.

The introduction of alternating positive and negative pressure pulses between the polyurethane diaphragm and the plastic case causes the sac to alternately collapse and then expand. This causes the sac to fill with blood when a negative pressure is applied, and to eject blood through the passageway when a positive pressure is applied. An electronic control means will detect the R-wave of the electrocardiagram and control the timing of the application of both positive and negative pressure pulses. By applying negative pressure during systole of the weak right ventricle, the device will fill with blood as the ventricle ejects. During right ventricular diastals, positive pressure is introduced into the device and the sac collapses, ejecting blood into the pulmonary artery. By its action, the device relieves the right ventricle of a large proportion of its pressure work load and at the same time provides the power necessary to augment pulmonary circulation. Only a single connection to the vascular system is required. The right ventricular assist device may be implanted in the thoracic cavity, or it may be placed in a paracorporeal position with the graft brought through the chest wall. The interior of the sac is well washed with blood and because of the highly non-thrombogenic characteristics of the segmented polyurethane, no anti-coagulants are required. The device of the present invention is simpler in both function and application then either the left ventricular assist pump (as used for right ventricular support) or the intra-aortic balloon/graft device. The device of the present invention provides a higher degree of circulatory assist for augmentation than does the intra-aortic balloon/graft device. While the augmentation is not as great as a left ventricular assist pump, the trauma to the blood is minimized, and only a single graft need be made in the pulmonary artery.

The right ventricular assist device of the present invention is designed to be capable of long term, that is, days to weeks of assistance in a patient with a closed incision.

The present invention is an improved modification of the device previously utilized as a left ventricular assist pump. The absence of valves and the single opening to the pulmonary artery substantially lessens the trauma to the patient when right ventricular assistance is needed.

DETAILED DESCRIPTION OF THE DRAWING

Figure 1:
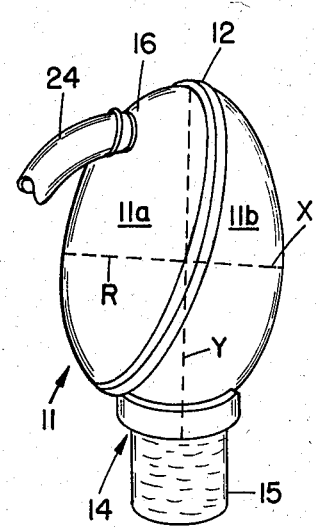
FIG. 1 is a isometric sketch of a right ventricular assist device constructed in accordance with the present invention.
Figure 4:
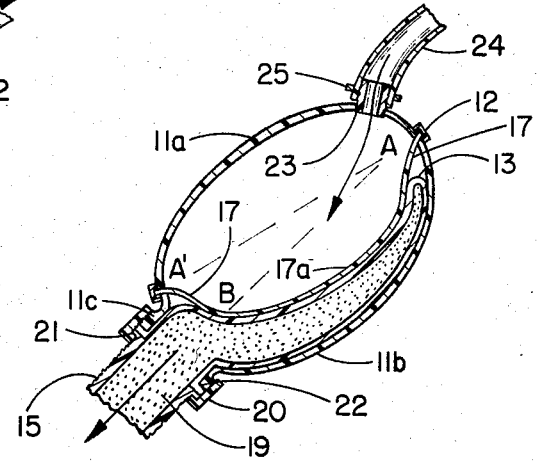
FIG. 4 is a diagrammatic cross sectional view of the present invention during discharge of the blood into the pulmonary artery.

As illustrated in FIG. 1, the right ventricular assist device of the present invention includes an oblate spheroid shell 11 formed of solid implantable plastic such as polycarbonate or polysulfone. The shell is formed in two halfs, 11a and 11b joined together by a clamp ring 12 which secures a flexible diaphragm 17 which is anchored about its perimeter to the clamping means 12, and extends across the spheroid, dividing it into two unequal portions. As illustrated in FIG. 4, the clamping ring 12 defines an elliptical plane A-A' which is tangent to the plane of the equator defined as A-B in FIG. 4. As will hereinafter be discussed in detail, the angle between A-A' and the equatorial plane A-B provides a sequential pumping action for expelling the blood from a segmented polyurethane sac 13, and simultaneously preventing the collapse of the sac 13 in such a manner as to trap or damage the blood therein.

The rigid ellipsoidal shell 11 defines a first opening 14 for a single valveless passageway 19 and a dacron graft 15 that extends from the pulmonary artery to the passageway 14 of the polyurethane sac 13. The ellipsoidal shell 11, also defines a second opening 16 for pressurizing an interior pumping portion defined between the shell portion 11a and diaphragm 17. Positioned within shell member 11, is a smooth seamfree ellipsoidal sac 13 formed of segmented polyurethane which receives blood to be circulated through a single valveless passageway 19 that defines both an inlet and an outlet passageway.

As illustrated in FIG. 1, the present invention defines an ellipsoidal shell having a transverse axis X and a longitudinal axis Y. A plane defined across the equator by axis X and Y is rotated about the Y axis as indicated by the radius R to define ellipsoidal volume. As illustrated in FIG. 1, the ellipsoid form, when the minor axis R is rotated, is deemed an oblate spheroid.

As illustrated in FIG. 4, the segmented polyurethane sac 13 is connected to the dacron graft 15 by means of a coupling which surrounds the inlet-outlet passageway 19. The shell member 11b defines an enlarged neck portion 11c having threads thereon for engaging a union nut 20 which clamps the graft to the passageway 14 by means of a clamp ring 21 formed on the end of the graft 15 and a heat set portion 22 defined on the end of the passageway 19. When union nut 20 is tightened about the threads on neck 11c, it clamps the dacron graft 15 tightly against the outwardly flared portion 22 of the polyurethane sac, thereby presenting a nearly seamfree surface for the blood which flows in and out of passageway 19.

An air fitting 23 threadably engages the smaller portion of the oblate spheroid 11a and provides a rigid surface for sealingly engaging a pneumatic hose 24 formed of polyvinyl chloride tubing. A clamp ring 25 secures the PVC tubing to the air fitting 23.

Figure 5:
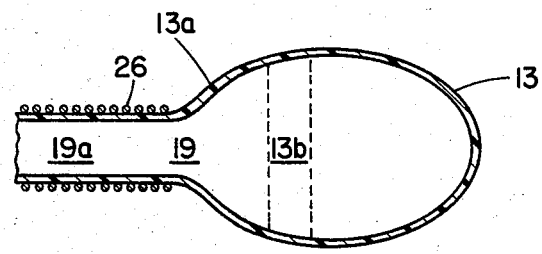
FIG. 5 is a cross sectioned diagrammatic sketch of a segmented polyurethane sac used in the present invention.

Two additional features for the segmented polyurethane sac are illustrated in FIG. 5. In the first of these features, a thickened neck portion 13a is provided immediately surrounding the valveless passageway 19. This thickened neck portion gradually reduces its diameter over a transition zone 13b to provide a wall thickness of approximately 0.30 inches for the wall of the sac as indicated at 13 in FIG. 5. The stiffened portion 13a prevents the collapse of the polyurethane sac about the discharge passageway 19 when the blood is being emptied therefrom as illustrated in FIG. 4. By preferentially collapsing the outer portion 13 of the sac, the blood is driven outwardly through the single inlet-outlet passageway 19 with the outer portion of the sac 13 being collapsed first.

FIG. 5 also illustrates a second embodiment for attaching the right ventricular assist device to the pulmonary artery. A dacron reinforcing means 26 may be applied to an extended neck portion 19a that forms an integral part of the polyurethane sac 13. This may take the form of a conventional dacron graft, or may be a simple flexible reinforcing structure such as a dacron knit. By providing a completely seamfree blood contacting surface from the anastomosis to the pumping chamber, the possibility of thrombus formation is completely eliminated. When the polyurethane sac illustrated in FIG. 5 is utilized, the dacron graft 15 is no longer necessary, and the extended neck portion 19a is anastomosed directly to the pulmonary artery as illustrated in FIG. 2.

Figure 2:
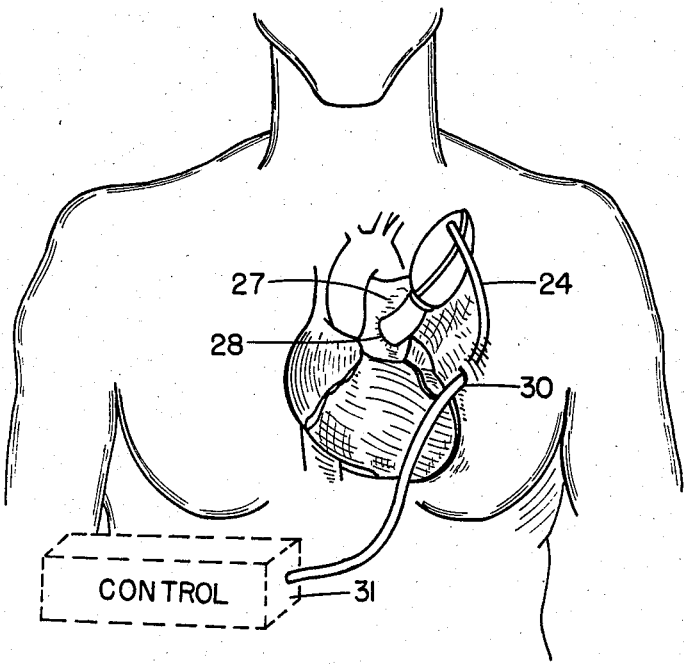
FIG. 2 is a sketch illustrating the installation of a right ventricular assist device on the pulmonary artery.

As illustrated in FIG. 2, the right ventricular assist device is anastomosed to the pulmonary artery with an end to side suture 28. The right ventricular assist device is located within the thoracic cavity, with the air tube 24 exiting the body through incision 30 and coupled directly to a control means 31.

The control unit 31 may be of a conventional type manufactured by Vitamek, Inc. of Houston, Tex. This unit includes a pressure and a vacuum pulser and a timing unit. A synchronizing unit may be used to actuate the pulser in response to the R-wave of the patients electrocardiagram.

OPERATION OF THE DEVICE

Figure 3:
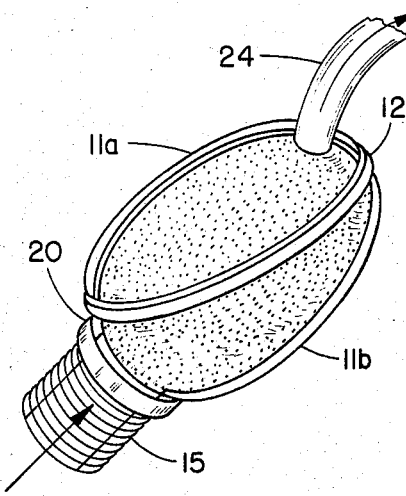
FIG. 3 is a cross section and schematic representation of the right ventricular assist device when filled with blood.

During the systole of a weak right heart ventricle, a negative pressure is applied by control unit 31 through tubing 24 to the interior cavity 11a of the right ventricular assist device. By applying a negative pressure, the device will fill with blood as the ventricle ejects as illustrated in FIG. 3.

During right ventricular diastole, a positive pressure is introduced in the device and the sac collapses as illustrated in FIG. 4 thereby ejecting blood into the pulmonary artery. By its action, the device relieves the right ventricle of a large proportion of its pressure work load and at the same time provides the power to augment pulmonary circulation.

As is noted in FIG. 2, the pulmonary artery trunk 27 is short, and provides only minimal room for grafting the single connection to the vascular system.

As illustrated in FIG. 4, a flexible diaphragm 17 forms an inverted domed surface 17a for ejecting the blood from the sac 13. The domed portion 17a of the diaphragm 17 is configured to prevent complete collapse of the segmented polyurethane sac 13. By design, the dome and diaphragm are configured to eject 80 to 90% of the blood present in sac 13. By preventing the complete collapse of the sac, it is possible to minimize hemolysis and blood trauma. When a negative pressure is drawn as illustrated in FIG. 3, the domed portion of diaphragm 17 is inverted upwardly against the upper portion of the shell 11a and allows the sac 13 to completely fill the enclosed volume defined by ellipsoidal shell 11.

As noted in FIG. 4, the diaphragm is mounted along an elliptical plane A-A' which is placed at an angle to the equatorial plane A-B. By angling the diaphragm 17 with respect to the equatorial plane, and placing the single inlet-outlet passageway 19 along the longitudinal axis of the equator, it is possible to provide for the maximum possible stroke ejection volume, while minimizing the formation of dead spots which trap blood, or the formation of areas in which the sac 13 would be collapsed upon itself, thereby causing additional blood trauma. By providing an angle between A-A' and A-B of 10° to 20°, the efficiency of the device is enhanced, while the trauma to the blood is decreased.

The sac and diaphragm are preferably fabricated from a plastic material. The segmented polyurethane material is available under the tradename, Biomer, a product marketed by Ethicon, Inc. of Summerville, N.J. The Biomer product is a partially crossed linked segmented co-polymer of tetramethylene glycol and methylene diphenyl isocyanate commercially available in a solution of N,N-dimethyl acetamide. Sac 13 is formed of a plurality of thin fused layers of segmented polyurethane in a manner similar to the sac previously disclosed in U.S. Pat. No. 4,222,127, the disclosure of which is hereby incorporated herein by reference. The sac of the present invention may be cast in a manner identical to the casting of the sac described in the aforementioned patent.

The right ventricular assist device has been surgically attached to goats and comparative tests were made between several methods of providing augmented right ventricular support. Profound right ventricular failure (RVF) was produced in sixteen healthy goats by inducing ventricular fibrillation after the systemic circulation was supported with a pneumatic pulsaltile left arterial (LA) to aorta bypass pump. Right arterial (RA) pressure was adjusted to 18±3 mmHg: blood pH, $pCO_2$, $pO_2$ and temperature were controlled. Four methods of providing pulmonary blood flow were evaluated in each animal.

| METHOD OF PROVIDING PULMONARY BLOOD FLOW | C.I. (ml/min/kg) | LA Pressure (mm Hg) | RA Pressure (mm Hg) |
|---|---|---|---|
| (1) Passive flow through the pulmonary artery (PA) due to RA to LA pressure gradient | 31.1 ± 12.9 | 0 ± 6 | 18 ± 3 |
| (2) Pulmonary artery pulsation (PAP) via a 40 ml intra-aortic balloon (IAB) within a 20 mm Dacron graft anastomosed to the main PA | 44.4 ± 13.6 | 3 ± 5 | 18 ± 3 |
| (3) PAP via a 65 ml single port valveless sac pulsatile assist device | 64.3 ± 16.9 | 5 ± 3 | 17 ± 4 |
| (4) RA to PA Bypass via a valved pneumatic pulsatile sac type pump | 102.0 ± 20.7 | 14 ± 5 | 12 ± 3 |

The passive pulmonary artery flow due (1) to the right arterial to left arterial pressure gradient provided inadequate pulmonary circulation. As indicated in the above table at (2), the addition of pulmonary arterial pulsation from a 40 ml intra-aortic balloon and a 20 mm dacron graft augmented the circulation 45% above the passive pulmonary artery flow.

The third set of test results utilizing a 65 ml single port valveless sac pulsatile assist device increased blood flow 65% over the pulmonary artery pulsation, and more than doubled the flow obtained passively through the pulmonary artery.

The last test (4) indicated as RA to PA bypass was provided from a valved right arterial to pulmonary artery bypass pump. This pump increased the circulatory flow 228%.

In profound right ventricular failure, the use of a bypass pump as illustrated in the fourth set of Figures would be the preferred method of pulmonary circulatory support. However, the present invention is particularly suited for augmenting or assisting a right ventricle after failure, after it is desired to wean the patients heart from the bypass pump. In a human being, the blood flow through the pulmonary artery of a normal health individual is approximately 5 liters per minute. Any flow below 3 liters per minute is deemed to be inadequate. By providing an 80 ml. sac, the present invention can provide two liters per minute of augmentation to assist the right ventricle. While the installation of an 80 ml device in the case of profound right ventricular failure would provide only marginally adequate flow, the installation of the device after partial recovery of the ventricle, would allow the ventricle to be assisted and recover to normal flow rates. Since the device may remain in the thoracic cavity for a period of days to weeks, it provides an opportunity for the patients heart to recover with a closed chest cavity.

The foregoing specification and drawing describes the preferred embodiment of the invention, it should be understood that various other modifications may be made therein without departing from the scope of the invention, that the scope of the invention be determined with reference to the following appended claims.

We claim:

1. A right ventricluar assist device for assisting the circulation of the blood, said device comprising:
   (a) a smooth seamfree ellipsoidal sac formed of segmented polyurethane for receiving blood to be circulated, said sac having a single valveless passageway to provide a single inlet and outlet,
   (b) a rigid ellipsoidal shell surrounding said sac, said shell having X, Y and R axes, wherein X and Y define an ellipse, and R defines a radius rotated to form the ellipsoid, said ellipsoid having a longitudinal axis and an equatorial plane, said shell having a first opening for said single valveless passageway generally aligned with said longitudinal axis and a second opening for pressurizing an interior portion of said shell,
   (c) A flexible diaphragm extending across the interior of said shell, said diaphragm providing a means for alternately expanding and collapsing said sac, said diaphragm dividing the interior of the ellipsoidal shell into two unequal volumes, with the sac and first opening in a first and larger volume, and the second opening and a pressurizing chamber defined in a second and smaller volume, the perimeter of said diaphragm defining an ellipitical plane that is angled with respect to said equatorial plane to expel at least 80% of the blood present in said sac as a positive pressure is supplied through said second opening, said diaphragm being angled and dimensioned to prevent the collapse of said sac when blood is expelled therefrom;
   (d) means for grafting the valveless passageway to a pulmonary artery.

2. A right ventricular assist device for assisting the circulation of blood as claimed in claim 1, wherein said ellipsoid is an oblate spheroid with said valveless passageway generally aligned with the longitudinal axis of the spheroid.

3. A right vertricular assist device for assisting the circulation of blood as claimed in claim 1 which further includes means for alternately pressurizing and evacuating said second and smaller volume, said pressurizing occurring during a diastole of the assisted ventricle.

4. A right ventricular assist device for assisting the circulation of blood as claimed in claim 1 which further includes an integral coupling means formed on said rigid ellipsoid, said coupling means joining said valveless passageway with a means adapted to be grafted to a living vessel.

5. A right ventricular assist device for assisting the circulation of blood as claimed in claim 2 wherein said second passageway is also generally aligned with the longitudinal axis of the spheroid opposite said single valveless passageway.

6. A right ventricular assist device for assisting the circulation of blood as claimed in claim 1 or 2 or 3 or 4 which further includes a stiffened region in said sac surrounding the valveless passageway.

7. A right ventricular assist device for assisting the circulation of blood as claimed in claim 2 or 3 or 4 or 5 wherein said diaphragm is also formed of segmented polyurethane with its perimeter defining a plane that is angled from 10° to 20° from a plane passing through the equator of the ellipsoid.

8. A right ventricular assist device for assisting the circulation of blood as claimed in claim 7 wherein a portion of said perimeter is generally tangential to the equatorial plane.

9. A right ventricular assist device for assisting the circulation of blood as claimed in claim 1 or 2 or 3 or 4 which further includes an elongate neck integrally formed with said sac to provide a smooth seamfree passageway from said pulmonary artery to said sac, said elongate neck having an external and flexible reinforcing means applied thereto.

10. A right ventricular assist device for assisting pulmonary arterial circulation, said device comprising:
    (a) a smooth seamfree sac formed of segmented polyurethane for receiving blood to be circulated, said sac having a single valveless passageway to provide a single inlet and outlet,
    (b) a two part rigid shell surrounding said sac, said shell defining an oblate spheroid with a longitudinal axis and an equatorial plane, said shell defining a first opening generally aligned with said longitudinal axis for receiving said single valveless passageway formed in said sac, the first part of said shell defining a blood pumping portion and the second part defining an air motor portion,
    (c) an angled pumping diaphragm mounted between the two parts of said rigid shell, with the perimeter of said diaphragm defining an elliptical plane that is angled from 10° to 20° with respect to said equatorial plane, said diaphragm having a reversable dome portion for collapsing said sac when said air motor portion is pressurized, said domed portion allowing for full expansion of said sac when said air motor portion is evacuated,
    (d) a means for anastomosing the valveless passageway to the pulmonary artery.

11. A right ventricular assist device for assisting pulmonary arterial circulation as claimed in claim 10 which further includes means for alternately pressurizing and evacuating said air motor portion, said evacuation occurring during right ventricular systole, and said pressurization occurring during right ventricular diastole.

12. A right ventricular assist device for assisting pulmonary arterial circulation as claimed in claim 10 which further includes an integral coupling means formed on the first portion of said shell, said coupling means joining said valveless passageway and a means adapted to be anastomosed to the pulmonary artery.

13. A right ventricular assist device for assisting pulmonary arterial circulation as claimed in claim 10 wherein said single valveless passageway defines an elongate and stiffened neck portion, said neck portion having an external reinforcing means for anastomosing said neck portion directly to said pulmonary artery.

14. A right ventricular assist device for assisting pulmonary arterial circulation as claimed in claim 10 or 11 or 12 or 13 which further includes a stiffened region of said sac surrounding an opening for the valveless passageway.

15. A right ventricular assist device for assisting pulmonary arterial circulation as claimed in claim 10 or 11 or 12 or 13 wherein said diaphragm is also formed of segmented polyurethane, with said angled elliptical plane being generally tangential to said equatorial plane.

* * * * *